US010285656B2

(12) United States Patent
Wang et al.

(10) Patent No.: US 10,285,656 B2
(45) Date of Patent: May 14, 2019

(54) X-RAY IMAGING SYSTEM AND METHOD

(71) Applicant: Carestream Health, Inc., Rochester, NY (US)

(72) Inventors: Xiaohui Wang, Pittsford, NY (US); Kevin J. Hobert, Pittsford, NY (US); David H. Foos, Webster, NY (US)

(73) Assignee: Carestream Health, Inc., Rochester, NY (US)

( * ) Notice: Subject to any disclaimer, the term of this patent is extended or adjusted under 35 U.S.C. 154(b) by 97 days.

(21) Appl. No.: 14/974,132

(22) Filed: Dec. 18, 2015

(65) Prior Publication Data
US 2016/0174918 A1   Jun. 23, 2016

Related U.S. Application Data

(60) Provisional application No. 62/093,443, filed on Dec. 18, 2014.

(51) Int. Cl.
*A61B 6/08* (2006.01)
*H05G 1/10* (2006.01)
*A61B 6/00* (2006.01)
*A61B 6/06* (2006.01)

(52) U.S. Cl.
CPC ............ *A61B 6/4405* (2013.01); *A61B 6/06* (2013.01); *A61B 6/08* (2013.01); *A61B 6/461* (2013.01); *A61B 6/467* (2013.01); *A61B 6/587* (2013.01); *A61B 6/588* (2013.01)

(58) Field of Classification Search
CPC .......... A61B 6/06; A61B 6/08; A61B 6/4405; A61B 6/461; A61B 6/467; A61B 6/587; A61B 6/588; A61B 6/508; A61B 5/0059; A61B 6/4021; A61B 6/4417; A61B 6/4423; A61B 6/5247; A61B 6/548; A61B 8/4472; A61B 8/565; A61B 5/0002; A61B 5/0091; A61B 5/4312; A61B 5/4528; A61B 6/502; A61B 8/00; A61B 8/0825; A61B 6/469; A61B 6/581; A61B 6/583; A61B 6/542; A61B 6/463; A61B 6/544; A61B 6/545; A61B 6/0407; A61B 6/4464; A61B 6/462; A61B 6/465; A61B 6/527; G21K 1/04; G21K 1/043; H05G 1/26; G01N 2223/076; G01N 2223/3308; G01N 2223/611; G01N 23/2206; G01N 23/223; G06K 2209/01
USPC ................. 378/4, 62, 102, 206, 205, 207
See application file for complete search history.

(56) References Cited

U.S. PATENT DOCUMENTS

| | | | |
|---|---|---|---|
| 7,198,404 B2 * | 4/2007 | Navab | A61B 6/5247 378/206 |
| 7,224,769 B2 * | 5/2007 | Turner | A61B 6/14 378/102 |
| 7,494,276 B2 * | 2/2009 | Borgmann | A61B 6/08 378/162 |
| 7,841,772 B2 | 11/2010 | Nishii et al. | |
| 8,989,352 B2 * | 3/2015 | Laws | A61B 6/08 378/145 |
| 9,125,623 B2 * | 9/2015 | Watanabe | A61B 6/5229 |
| 9,974,504 B2 * | 5/2018 | Lee | A61B 6/462 |

(Continued)

*Primary Examiner* — Irakli Kiknadze

(57) ABSTRACT

An X-ray imaging system uses an X-ray source to emit an X-ray beam for exposing a desired radiation field. A camera is configured to capture a current image of the radiation field and to display a current image of the radiation field before the exposure is activated.

22 Claims, 7 Drawing Sheets

(56) References Cited

U.S. PATENT DOCUMENTS

| | | | |
|---|---|---|---|
| 2003/0185348 A1* | 10/2003 | Ghelmansarai | A61N 5/1049 378/206 |
| 2006/0114987 A1* | 6/2006 | Roman | H04N 7/142 375/240.01 |
| 2007/0230659 A1* | 10/2007 | Turner | G03B 42/02 378/63 |
| 2009/0060145 A1 | 3/2009 | Tranchant et al. | |
| 2011/0249799 A1* | 10/2011 | Lalena | A61B 6/08 378/97 |
| 2014/0362975 A1* | 12/2014 | Garcia | A61B 6/4283 378/62 |
| 2015/0223767 A1* | 8/2015 | Sehnert | A61B 6/06 378/42 |

\* cited by examiner

X-RAY IMAGING SYSTEM AND METHOD

CROSS REFERENCE TO RELATED APPLICATIONS

This application claims priority to U.S. Patent Application Ser. No. 62/093,443, filed Dec. 18, 2014, in the name of Wang, et al., and entitled IMPROVED X-RAY IMAGING SYSTEMS AND DEVICES.

This application is related in certain respects to U.S. patent application Ser. No. 13/083,860, filed Apr. 11, 2011, in the name of Lalena, et al., and entitled TUBE ALIGNMENT FOR MOBILE RADIOGRAPHY SYSTEM; U.S. patent application Ser. No. 13/284,218, filed Oct. 28, 2011, in the name of Lalena, et al., and entitled PROJECTOR AS COLLIMATOR LIGHT; and U.S. patent application Ser. No. 12/906,192, filed Oct. 18, 2010, in the name of Wendlandt, et al., and entitled MOBILE RADIOGRAPHY UNIT HAVING COLLAPSIBLE SUPPORT COLUMN, all three of which are incorporated herein by reference in their entirety.

FIELD OF THE INVENTION

The subject matter disclosed herein relates to radiographic imaging systems, devices, and methods. In particular, the systems and devices include a camera based device whereby an operator positions an X-ray source using a display screen that displays an X-ray source view.

BACKGROUND OF THE INVENTION

In some X-ray systems, when positioning the X-ray source assembly, or making minor adjustments thereto, such as in a larger wall system or smaller mobile system, the operator usually positions the X-ray source assembly based on the operator's point of view of the subject and the angle of the X-ray source assembly. The operator then adjusts his or her point of view by moving to a different location to check from another perspective whether the alignment between the X-ray source assembly and the subject is acceptable. Operator workflow would be improved by reducing requirements for the operator to reposition himself or herself to check the alignment. A camera based visual alignment system having a field of view coincident with an X-ray beam would be advantageous in this environment.

Some X-ray generators may be manufactured in a size small enough to fit in hand held devices. Some of these X-ray devices utilizing carbon nanotubes (CNTs) as a cathode which emit electrons when exposed to an electrical field. The CNT X-ray sources are lighter, smaller, work faster, operate at cooler temperatures, and use less peak power than the conventional systems. A hand-held X-ray system using a camera based visual alignment system having a field of view coincident with an X-ray beam would provide a convenient imaging system.

The discussion above is merely provided for general background information and is not intended to be used as an aid in determining the scope of the claimed subject matter.

BRIEF DESCRIPTION OF THE INVENTION

An X-ray system utilizing a visible light video or still image camera may be configured to capture and display the same or slightly larger field-of-view as the light beam of a collimator light. The video from the camera may be transmitted to a display screen, preferably situated on the X-ray source assembly that is facing the operator, to help the operator center the X-ray source position for proper X-ray exposure. The camera may also be mounted on the X-ray source assembly and use the X-ray source assembly as an optical reference object for aiming and centering the X-ray source. Similar structural arrangements may be used to simulate the view as seen looking down from the X-ray source assembly as the reference point of view.

An X-ray imaging system uses an X-ray source to emit an X-ray beam for exposing a desired radiation field. A camera is configured to capture a current image of the radiation field and to display a current image of the radiation field before the exposure is activated.

In one embodiment, a portable imaging apparatus has an X-ray source configured to emit an X-ray beam and a collimator proximate the X-ray source to define an X-ray radiation field to be exposed. A camera is included for capturing an optical image of the radiation field, and a display connected to the camera displays the image of the radiation field.

In another embodiment, a mobile X-ray imaging apparatus includes an X-ray assembly comprising a camera having a field of view coincident with a central axis of an X-ray beam emitted by an X-ray source. The camera captures a video image of a radiation field as the X-ray assembly is selectively positioned so that the radiation field coincides with a desired imaging area. A display screen in electrical communication with the camera receives and displays the video captured by the camera including the desired imaging area.

In another embodiment, a method of operating an X-ray system is disclosed. An X-ray source in a hand-held X-ray source assembly is activated and a radiographic image is captured in a digital detector exposed by the activated X-ray source. The digital detector transmits the captured radiographic image to the hand-held X-ray source assembly and is displayed on its display screen.

The summary descriptions above are not meant to describe individual separate embodiments whose elements are not interchangeable. In fact, many of the elements described as related to a particular embodiment can be used together with, and possibly interchanged with, elements of other described embodiments. Many changes and modifications may be made within the scope of the present invention without departing from the spirit thereof, and the invention includes all such modifications. The drawings below are intended to be drawn neither to any precise scale with respect to relative size, angular relationship, relative position, or timing relationship, nor to any combinational relationship with respect to interchangeability, substitution, or representation of a required implementation.

This brief description of the invention is intended only to provide a brief overview of subject matter disclosed herein according to one or more illustrative embodiments, and does not serve as a guide to interpreting the claims or to define or limit the scope of the invention, which is defined only by the appended claims. This brief description is further provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. The drawings are not necessarily to scale, emphasis generally being placed upon illustrating the features of certain embodiments of the invention. In the drawings, like numerals are used to indicate like parts throughout the various views. Thus, for further understanding of the invention, reference can be made to the following detailed description, read in connection with the drawings in which.

DETAILED DESCRIPTION OF THE INVENTION

Figure 1:
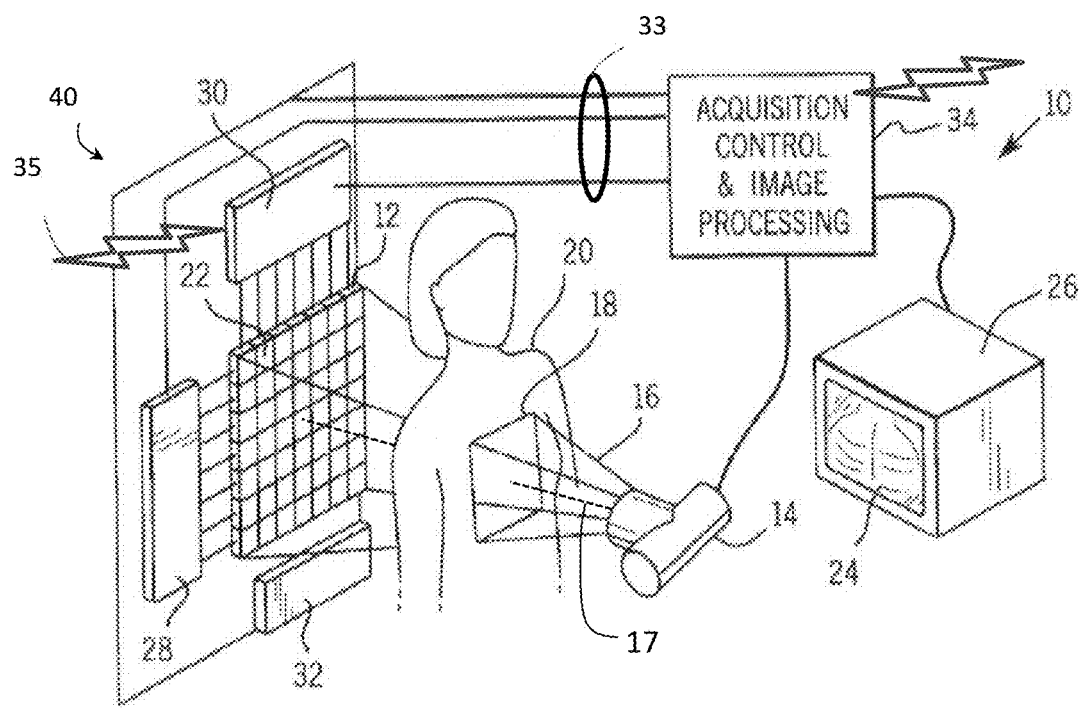
FIG. 1 illustrates an exemplary digital X-ray system.

FIG. 1 is a perspective view of a digital radiographic (DR) imaging system 10 that includes a generally planar DR detector 40 (shown without a housing for clarity of description), an X-ray source assembly 14 configured to generate radiographic energy (X-ray radiation), and a digital monitor 26 configured to display images captured by the DR detector 40, according to one embodiment. Although the DR detector 40 is depicted in FIG. 1 as a large panel detector, embodiments of the DR detector 40, described herein, may include smaller dimensions such that the DR detector 40 may be inserted intra orally for dental radiographic imaging. The DR detector 40 may include a two dimensional array 12 of detector cells 22 (photosensors), arranged in electronically addressable rows and columns. The DR detector 40 may be positioned to receive X-rays 16 passing through a subject 20 during a radiographic energy exposure, or radiographic energy pulse, emitted by the X-ray source assembly 14. As shown in FIG. 1, the radiographic imaging system 10 may use an X-ray source assembly 14 that emits collimated X-rays 16, e.g. an X-ray beam, selectively aimed at and passing through a preselected radiation field 18 of the subject 20. The X-ray source assembly 14 may include a light source and a digital video or digital still image camera in certain embodiments, as described herein. The emitted X-ray beam 16 may be attenuated by varying degrees along its plurality of rays according to the internal structure of the subject 20, which attenuated rays are detected by the array 12 of photosensitive detector cells 22. The planar DR detector 40 is positioned, as much as possible, in a perpendicular relation to a substantially central ray 17 of the plurality of rays 16 emitted by the X-ray source assembly 14. The substantially central ray 17 may be said to coincide with a central axis of the X-ray beam, as described herein. The array 12 of individual photosensitive cells (pixels) 22 may be electronically addressed (scanned) by their position according to column and row. As used herein, the terms "column" and "row" refer to the vertical and horizontal arrangement of the photosensor cells 22 and, for clarity of description, it will be assumed that the rows extend horizontally and the columns extend vertically. However, the orientation of the columns and rows is arbitrary and does not limit the scope of any embodiments disclosed herein. Furthermore, the term "subject" may be illustrated as a human patient in the description of FIG. 1, however, a subject of a DR imaging system, as the term is used herein, may be a human, an animal, an inanimate object, or a portion thereof.

In one exemplary embodiment, the rows of photosensitive cells 22 may be scanned one or more at a time by electronic scanning circuit 28 so that the exposure data from the array 12 may be transmitted to electronic read-out circuit 30. Each photosensitive cell 22 may independently store a charge proportional to an intensity, or energy level, of the attenuated radiographic radiation, or X-rays, received and absorbed in the cell. Thus, each photosensitive cell, when read-out, provides information defining a pixel of a radiographic image 24, e.g. a brightness level or an amount of energy absorbed by the pixel, that may be digitally decoded by image processing electronics in an image processing unit 34 and transmitted to be displayed by the digital monitor 26 for viewing by a user. An electronic bias circuit 32 is electrically connected to the two-dimensional detector array 12 to provide a bias voltage to each of the photosensitive cells 22.

Each of the bias circuit 32, the scanning circuit 28, and the read-out circuit 30, may communicate with an acquisition control and image processing unit 34 over a connected cable (wired) 33, or the DR detector may be equipped with a wireless transmitter to transmit radiographic image data wirelessly 35 to the acquisition control and image processing unit 34. As described hereinbelow, the X-ray source assembly 14 may also include a wired or wireless transmitter and/or receiver to receive digital images directly from the DR detector 40 or from the image processing unit 34. The acquisition control and image processing unit 34 may include a processor and electronic memory (not shown) to control operations of the DR detector 40 as described herein, including control of circuits 28, 30, and 32, for example, by use of programmed commands transmitted to the DR detector 40. It is commonplace to provide a processor and electronic memory within the housing (not shown) of the DR detector 40 to control its operations as described herein, including control of circuits 28, 30, and 32, for example, by use of programmed instruction stored in electronic memory of the DR detector 40. The processing carried out by the DR detector 40 may include filtering of dark images and image correction procedures to generate and store, or transmit, a final radiographic image capable of being displayed without requiring further processing. The acquisition control and image processing unit 34 may also be used to control activation of the X-ray source assembly 14 during a radiographic exposure, controlling an X-ray source electric current magnitude, and thus the fluence of X-rays in X-ray beam 16, and/or the X-ray source voltage, and thus the energy level of the X-rays in X-ray beam 16.

The acquisition control and image processing unit 34 may transmit image (pixel) data to the monitor 26, by cable or wirelessly, based on the radiographic exposure data received from the array 12 of photosensitive cells 22. Alternatively, acquisition control and image processing unit 34 can process the image data and store it, or it may store raw unprocessed image data, in local or remotely accessible memory.

With regard to a direct detection embodiment of DR detector 40, the photosensitive cells 22 may each include a sensing element sensitive to X-rays, i.e. it absorbs X-rays and generates an amount of charge carriers in proportion to a magnitude of the absorbed X-ray energy. A switching element may be configured to be selectively activated to read out the charge level of a corresponding X-ray sensing element. With regard to an indirect detection embodiment of DR detector 40, photosensitive cells 22 may each include a sensing element sensitive to light rays in the visible spectrum, i.e. it absorbs light rays and generates an amount of charge carriers in proportion to a magnitude of the absorbed light energy, and a switching element that is selectively activated to read the charge level of the corresponding sensing element. A scintillator, or wavelength converter, is disposed over the light sensitive sensing elements to convert incident X-ray radiographic energy to visible light energy.

Examples of sensing elements used in sensing array 12 include various types of photoelectric conversion devices (e.g., photosensors) such as photodiodes (P-N or PIN diodes), photo-capacitors (MIS), photo-transistors or photoconductors. Examples of switching elements used for signal read-out include MOS transistors, bipolar transistors and other p-n junction components.

Figure 2A:
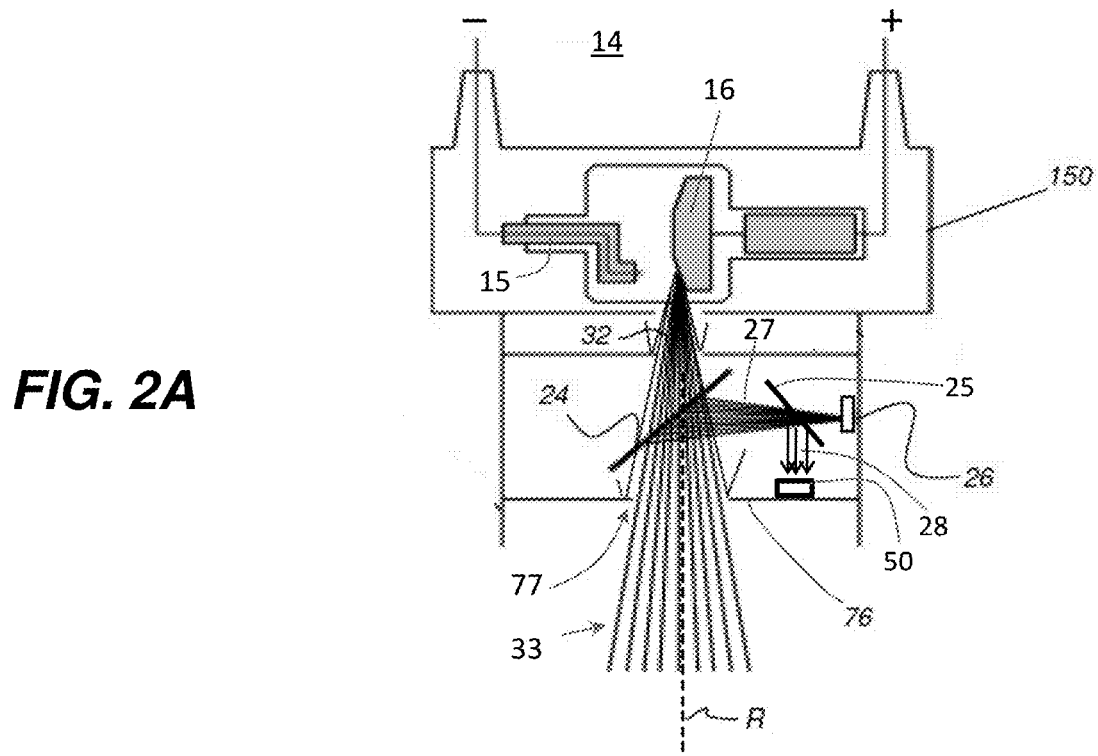
FIGS. 2A-2B are schematic diagrams of an exemplary X-ray assembly and X-ray source, respectively.

Referring to FIG. 2A, there are illustrated different embodiments of the X-ray source assembly 14 having an X-ray source 150. When power is applied to the X-ray source 150 via electric terminals +/−, a cathode 15 emits electrons toward a rotating anode 16 to generate X-rays 32. The generated X-rays 32 pass through an aperture 77 of an adjustable collimator 76 to shape the emitted X-rays into a directed X-ray beam 33. The area of a target of the X-ray beam may be referred to as a radiation field, such as on a subject to be exposed to X-ray beam 33. The radiation field may have its dimensions controlled by adjustment of one or more collimator blades (not shown) in orthogonal x and y directions to shape a size of the aperture 77. A light source 26, which may be referred to herein a collimator light, may project visible light 27 reflected by a mirror 24 to coincide with the X-rays 32 of the X-ray source 150. The light source 26 may comprise a light bulb, light emitting diode (LED), or other solid-state light source, and may be mounted inside the X-ray assembly 14. Thus, the visible light 27 is also shaped by the collimator 76 to illuminate the radiation field, to be exposed by the X-ray beam, with visible light in a size and shape substantially equivalent to that of the radiation field of the X-ray beam. The light source 26 and the mirror 24 may be precisely positioned so that a central axis of the light reflected from the mirror 24 is substantially coaxial with a central axis R of the X-ray beam 33. The mirror 24 may be made from a radiolucent material to allow transmission of the X-rays 32 therethrough without substantial interference, and while also reflecting the visible light rays 27 from light source 26. The light source 26 and/or the mirror 24 may be movably adjustable to project light 27 to form a visible illuminated area on a subject of a size that is greater than, less than, or equal to the area of the radiation field.

A still image or video camera 50 may be mounted within the X-ray assembly 14 together with a one-way mirror 25. Optical light 28 from objects outside the X-ray assembly 14 that are aligned proximate the central axis R may travel through the aperture 77 and be reflected by mirrors 24, 25 toward the camera 50. Thus, the camera 50 may capture still or video images of objects proximate the central axis R of the X-ray beam 33, which central axis R coincides with a center of the radiation field to be exposed by the X-ray beam 33 and illuminated by visible light 27. Thus, attachment of the camera 50 to the X-ray assembly 14 may be configured to be aligned with the visible light 27 from the light source 26 so that its field of view is substantially centered on the central axis of the visible light rays 27 and thus simultaneously aligned with the central axis R of the X-ray beam 33. In another embodiment, the positions of the camera 50 and the light source 26 may be swapped. A wired or wireless transmitter may be provided in the X-ray assembly 14 coupled to the camera to transmit video of the illuminated area to a display 26 and viewed on a display screen 24. The operator of the X-ray system 10 may view the display screen 24 while guiding and properly positioning the X-ray source assembly 14 to expose the desired radiation field of a subject for radiographic image capture. The operator may view the display screen 24 to insure that the illuminated area coincides with the desired radiation field of the subject before activating an X-ray exposure. Although the display 26 is shown as a standalone display 26 in FIG. 1, in another embodiment it may be conveniently attached to the X-ray assembly 14 for easy viewing by the operator while the operator manually positions the X-ray source assembly. The X-ray source assembly may also be configured to be positioned using automatic or manual motor control.

Figure 2B:
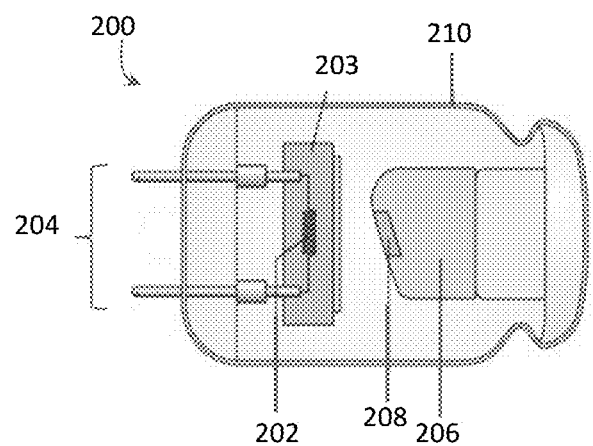

Referring to FIG. 2B, there is illustrated an embodiment of an X-ray source 150 in the form of an X-ray source 200 that may be advantageously utilized in a hand held X-ray device as described herein. The X-ray source 200 may be positioned as the X-ray source 150 as illustrated in FIG. 2A. The X-ray source 150 may comprise a tungsten filament 202, on the cathode side, secured in a focusing cup 203, and is energized by a current provided through terminals 204, generating emission of electrons from the filament 202. The anode side may include a stem 206 securing an electron target 208, made from tungsten, that emits X-rays upon impact from the emitted electrons. The assembly just described may be secured within an evacuated glass container 210. The X-rays travel substantially in the same path as the collimated X-ray beam shown in FIG. 2A and may be constructed within the X-ray assembly 14.

Figure 3:
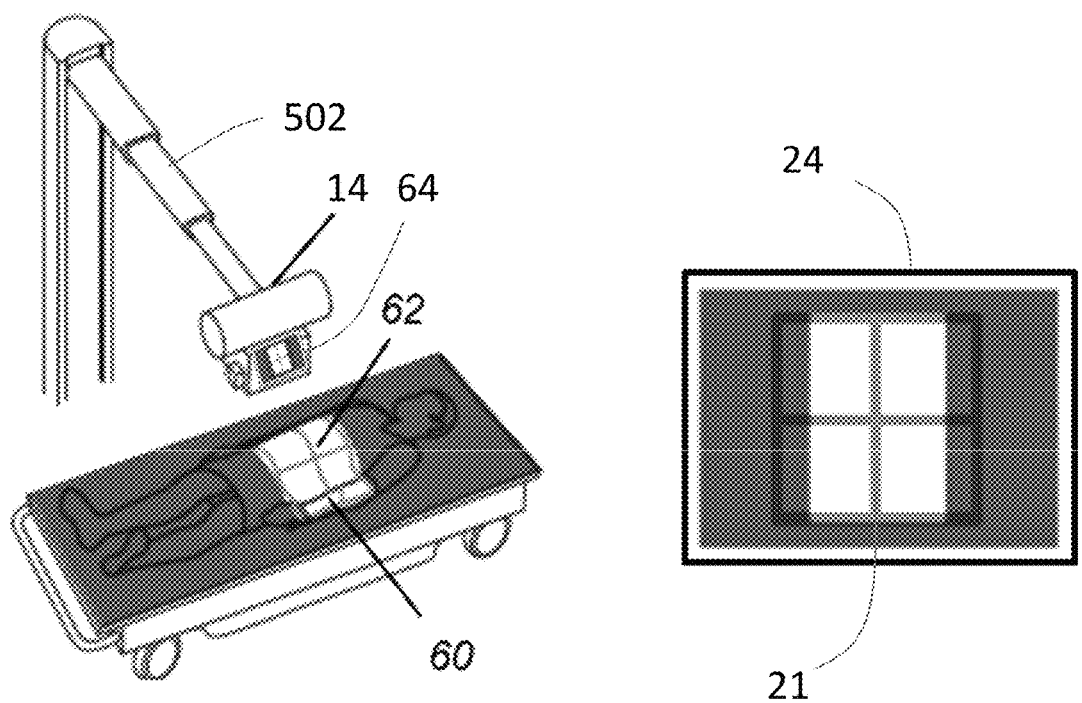
FIG. 3 illustrates an exemplary support arm system for securing an X-ray assembly and a display screen.

Referring to FIG. 3, there is illustrated an embodiment of the X-ray assembly 14 that may emit X-rays 32 that expose a radiation field 62 on a subject 60 to be imaged. The X-ray assembly 14 may be mounted on support arm 502 that is attached to a mobile cart X-ray system or to a fixed wall mounted X-ray system. The support arm may be adjustable in three dimensions or it may be substantially fixed with limited movement. The support arm may be part of an adjustable column on a rolling (mobile) X-ray system or it may be a fixed column mobile system. The radiation field 62 may have its dimensions controlled by adjustment of one or more collimator blades of the X-ray assembly 14 in orthogonal x and y directions. A light source 26, as described herein, may project visible light 27 reflected by a mirror 24 to coincide with the X-rays 32 of the X-ray assembly 14 and illuminate the projected radiation field 62 on the subject 60 with visible light 27 prior to exposing the subject 60 to the X-rays 32. As described above, a camera within the X-ray assembly may capture a still or moving image (video) of the radiation field and transmit the image for display on a display screen 24 as shown on the right of FIG. 3. The operator may view the display 24 to insure that the illuminated area coincides with the desired radiation field on the subject 60 before activating an X-ray exposure. Rather than a standalone display screen 24 as illustrated in FIG. 1, the display screen 64 may be conveniently attached to the X-ray assembly 14 as shown in FIG. 3. As shown in the display 24 of FIG. 3, the light source 26 may include a cursor 21 in the shape of a crosshair that is projected onto the radiation field to indicate where a central axis R of the X-ray beam 33 is targeted.

Figure 4A:
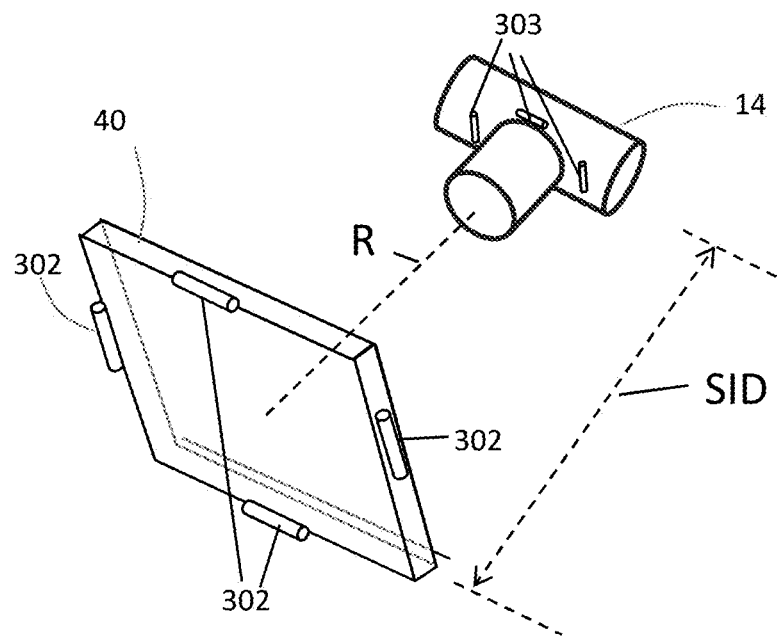
FIGS. 4A-4B are schematic diagrams of a DR detector position detection system.
Figure 4B:
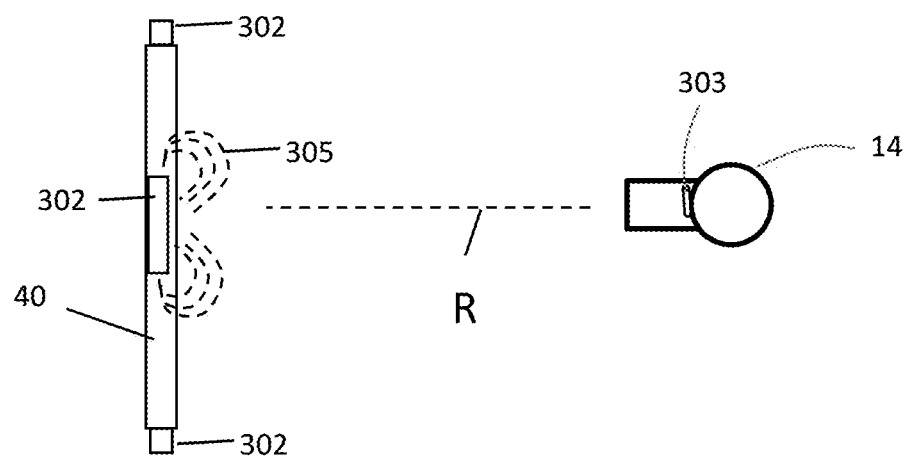

The transparent perspective view of FIG. 4A and side view of FIG. 4B illustrate positional detection devices that allow the X-ray assembly 14 to detect the spatial position of the DR detector 40 relative to the X-ray assembly 14. One or more transmitters 302 on the DR detector 40 may transmit signals detectable by sensors 303 attached to the X-ray assembly 14. In the embodiment shown in FIGS. 4A and 4B, a DR detector 40 may have attached thereto, or embedded therein, one or more transmitters 302 such as electromagnetic coils that generate an electromagnetic field or signal that is detected by one or more sensors 303, shown mounted on the X-ray assembly 14. In one embodiment, transmitters 302 may include inclinometers for detecting a positional orientation and transmit positional orientation data to X-ray assembly 14 which may be processed for determining relative spatial position.

It can be appreciated by those skilled in the position-sensing arts that there are a number of possible configurations that can be used as sensor apparatus 40 for position sensing and for providing data for angle, source-to-image-distance (SID) data, data for tracing the DR detector 40 outline, and centering data, when the DR detector 40 is positioned behind or underneath a patient or other object, or if the DR detector 40 is in the form of an intra oral detector. Centering data relates to the position of the center of DR detector 40 which may be used to generate a cursor on a display screen 24 that indicates the center of the DR detector 40. The centering data may also be used in combination with other known data related to the size, orientation, and shape of the DR detector 40 to generate cursors of various shapes on display screen 24. Source-to-image distance (SID), here the distance between the X-ray assembly 14 and the DR detector 40 may also be determined.

The transmitter 302 may transmit an analog signal or signals or one or more data values, for example. Position signals 305 can be sent from any of a number of transmitters, including inclinometers, radio-frequency devices, electromagnetic coils, and audio or ultrasonic signals, for example. Transmitters 302 and sensors 303 may be located at edges of their respective devices or may be integrated therewithin. In one embodiment, a processor may be utilized in the X-ray assembly 14 to process received positioning signals.

It can be appreciated that any number of possible arrangements of transmitters and sensors may be used in an arrangement similar to that shown in FIGS. 4A-4B for determining parameters such as angular orientation, aim centering, source-to-image distance (SID), and other variables that are of interest for obtaining a suitable radiographic image, whether for a mobile, hand held, or fixed-position radiography system. It can be appreciated by those skilled in the position-sensing arts that there are a number of possible configurations that can be used with transmitter/sensor combinations for position sensing and for providing data for angle, SID, data for tracing the DR detector 40 outline, and centering information where DR detector is positioned intra-orally, behind, or underneath a patient.

Figure 5A:
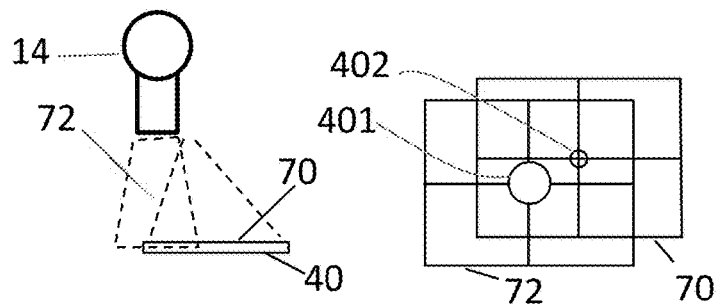
FIGS. 5A-5D are illustrations of X-ray assembly and DR detector misalignment indicators.
Figure 5B:
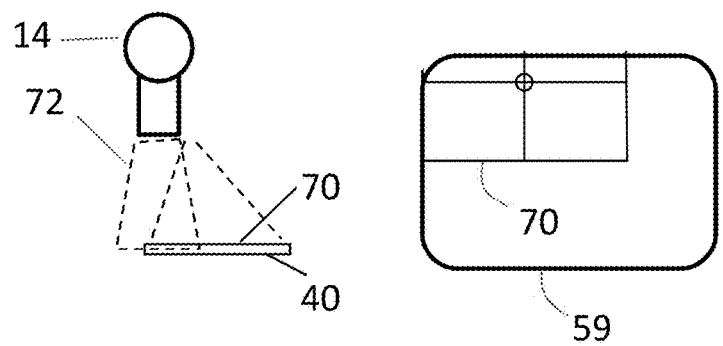
Figure 5C:
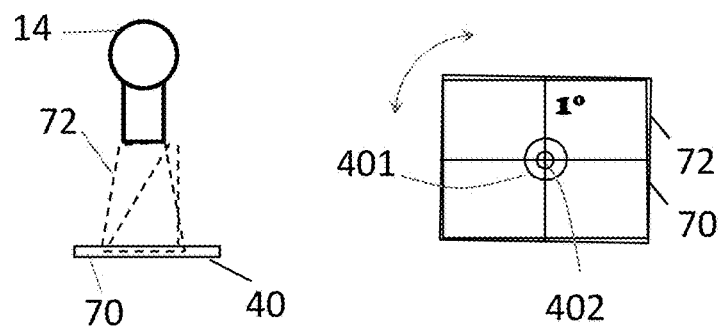
Figure 5D:
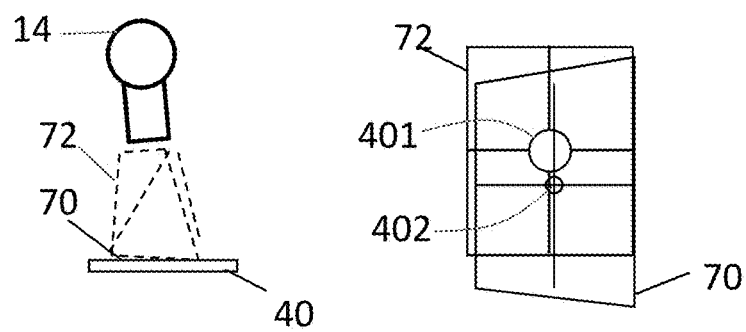

The positional relationship as between the DR detector 40 and the X-ray assembly 14 may be indicated on the display screen 24. FIGS. 5A-5D illustrate an example of a fixed cursor 72 that may be displayed on display screen 24 and the detected position 70 of the DR detector 40, also illustrated as a rectangle, as determined by the transmitter/sensor embodiments of FIG. 3A-3B. By way of example, FIG. 5A illustrates a graphic that may be shown on the display screen 24 demonstrating an off-center alignment whereby a center 401 of the radiation field (approximate central axis of the X-ray beam 33) is not aligned with a center 402 of the DR detector 40. Alternatively, FIG. 5B illustrates an embodiment whereby the physical dimensions 59 of the display screen may be used for graphically illustrating the detected position of the DR detector 40 relative to a center of the display. The center of the display may be configured to coincide with the central axis R of the X-ray beam 33 and thereby the center of the radiation field. FIG. 5C illustrates a graphic that may be shown on the display screen 24 demonstrating a 1° rotational misalignment, whose numerical value may be shown on the display screen 24. FIG. 5D illustrates a graphic that may be shown on the display screen 24 demonstrating a skewed alignment whereby a tilt of the X-ray assembly 14 relative to the DR detector 40 may be corrected by adjusting their relative angle. In a relative position, the X-ray assembly 14 source is nearly centered with respect to DR detector 40, but the angle is skewed from normal. Detected position 70 is accordingly non-rectangular, such as having a keystone pattern, indicating the angular relationship of the radiation path. The patterns shown at 70 and 72 are representative examples selected for illustration and can take any of a number of forms, including, but not limited to, crosshair patterns, including crosshair patterns with or without a central circle as shown in the example of FIGS. 5A-5C.

Figure 6A:
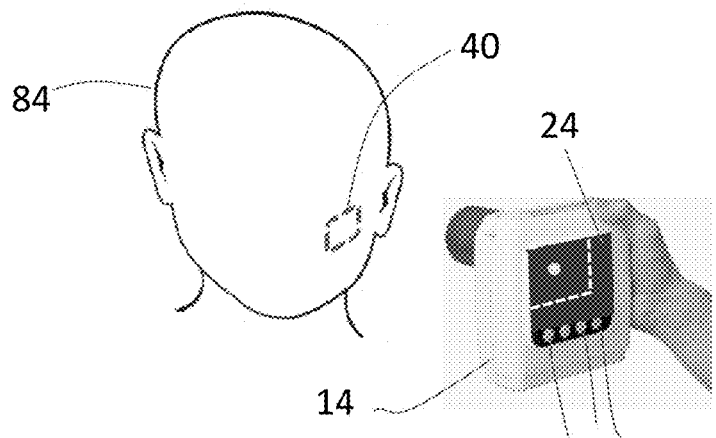
FIGS. 6A-6C are diagrams illustrating a hand-held X-ray system and operation thereof.
Figure 6B:
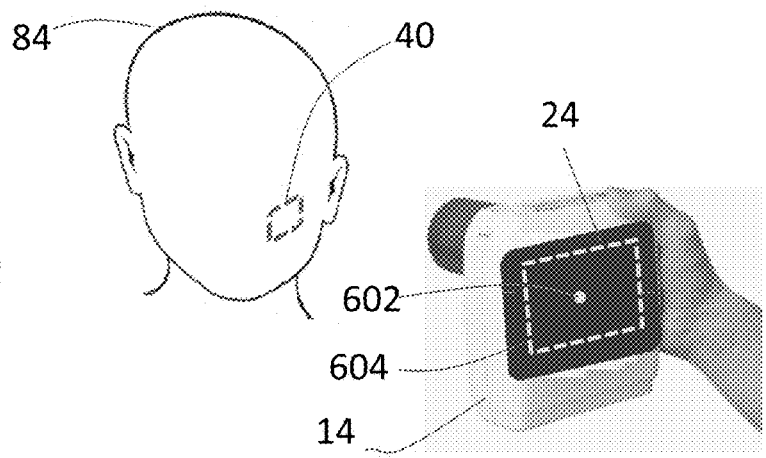
Figure 6C:
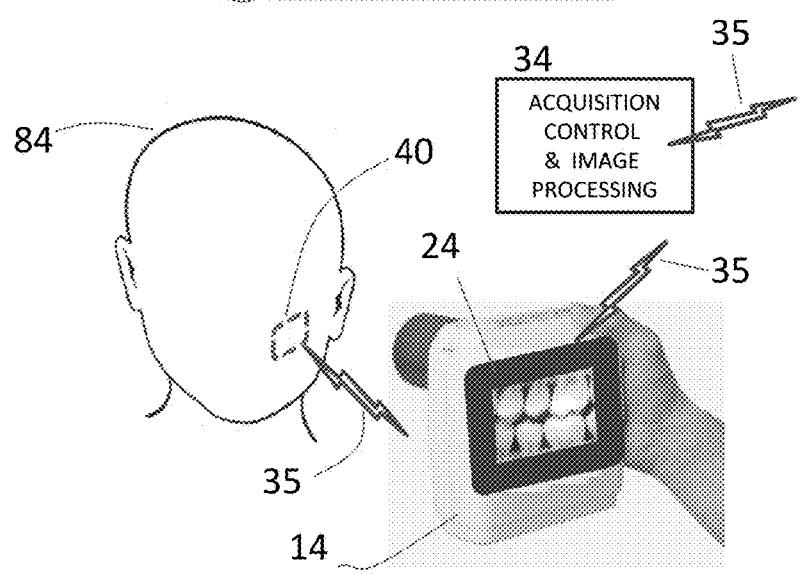

Turning to FIGS. 6A-6C, there is illustrated an embodiment, in FIG. 6A, whereby the X-ray assembly 14 comprises a hand-held size and contour with a display screen 24 that is mounted in a rearward facing side of the hand held X-ray assembly 14. The forward facing X-ray source of the hand-held X-ray assembly is aimed to expose a patient 84. The hand-held X-ray assembly 14 may includes image processing electronics similar to those contained in the DR detector 40 or the image processing unit 34 as described in relation to FIG. 1. The hand-held X-ray assembly 14 may further include knobs, or buttons, 86 to control operation of the hand-held X-ray assembly 14, or the controls may comprise touch controls formed as a touch screen version of the display screen 24. The hand-held X-ray assembly 14 may include a battery therewithin for operating the hand-held X-ray assembly or it may include a cable connector for receiving operating power from a central power source, or a combination thereof. FIG. 6A illustrates an intra-oral embodiment of the DR detector 40 described herein which is not visible to the naked eye as the patient 84 has positioned the DR detector intra-orally with mouth closed. Using built-in embodiments of the transmitter/sensor configurations described herein with respect to FIGS. 4A-4B, the display screen 24 may show that the center 602 of the DR detector 40 is not centered in the display screen 24 and so would not be aligned with a center of the X-ray beam, or, using the alternative cursor 604, as outline of the DR detector 40, that a portion of the outline of the DR detector falls outside the display screen 24 and thereby may be outside the radiation field of the emitted X-ray beam. The DR detector centering information may be shown on the display screen 24, as an example, or an outline of the DR detector 40 may be shown, or other styles of cursor.

FIG. 6B illustrates a satisfactory alignment of the hand-held X-ray assembly 14 with the DR detector 40 as the cursor 602 is centered in the display, or, alternatively, the outline cursor 604 appears entirely within the borders of the display screen 24. When the DR detector 40 is properly centered the hand-held X-ray assembly 14 may be triggered by the operator to fire an X-ray pulse, whereby the intra-oral DR detector 40 may capture a radiographic image of dental structures of the patient 84. In one embodiment, illustrated in FIG. 6C, the intra-oral DR detector 40 includes a microcontroller controlling a transmitter that may transmit 35 the captured image to the hand-held X-ray assembly 14 for display on its built-in display screen 24, or it may be transmitted 35 to the acquisition & image processing unit 34 for image processing, which then transmits 35 the captured radiographic image to the hand-held X-ray assembly 14 to be displayed thereon, as shown in FIG. 6C.

Figure 7:
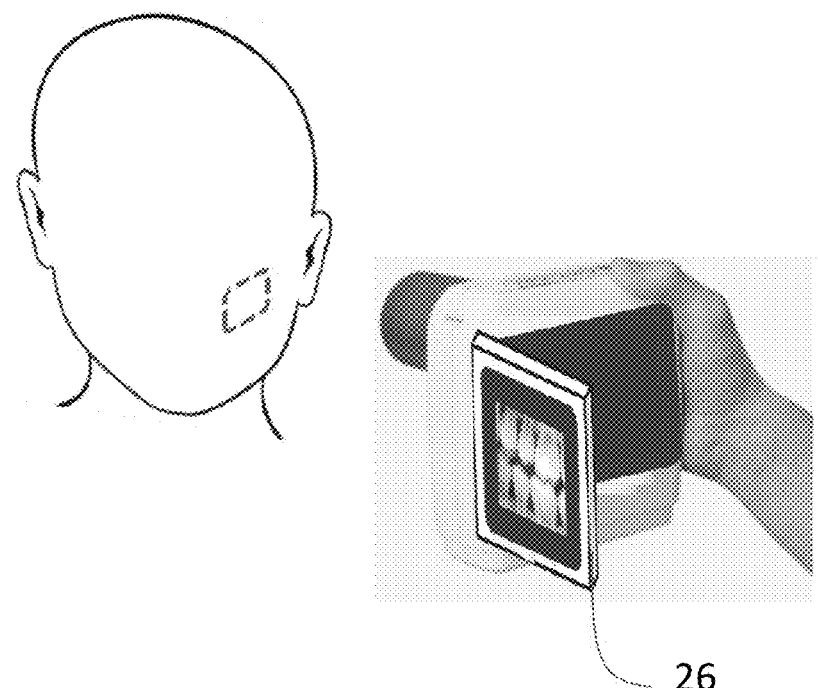
FIG. 7 illustrates a feature of the hand-held X-ray assembly of FIGS. 6A-6C.
Figure 8:
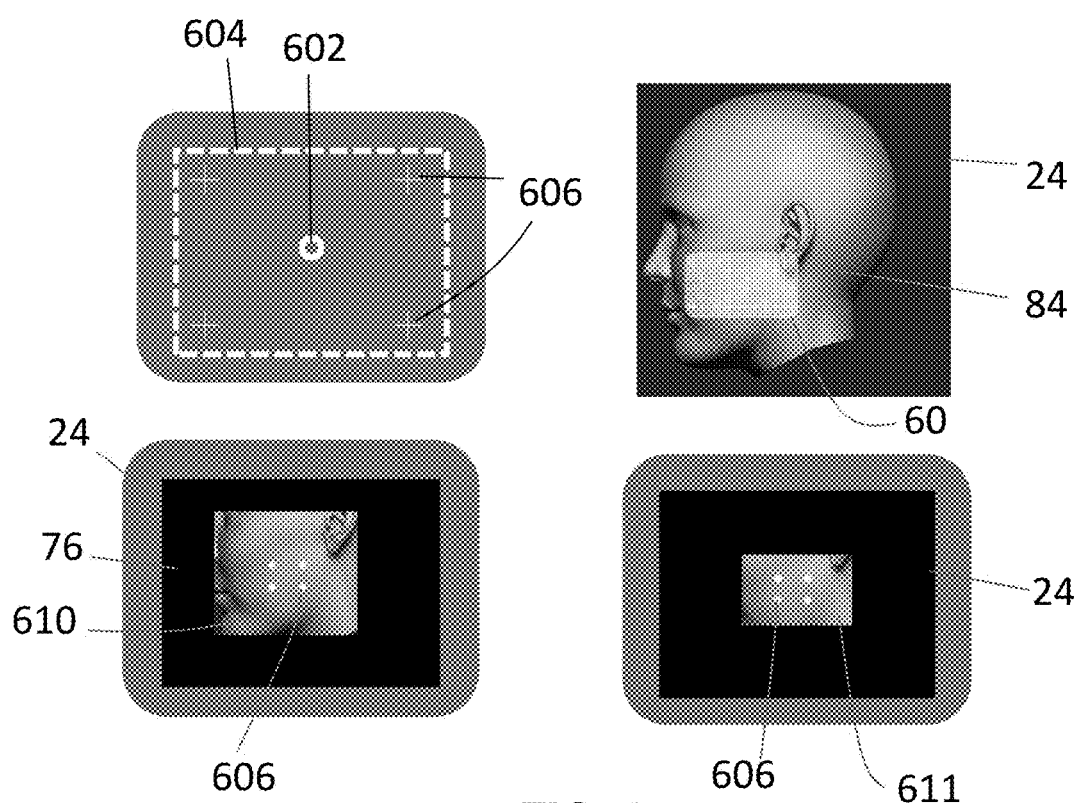
FIG. 8 illustrates display features of the hand-held X-ray assembly of FIGS. 6A-6C.

FIG. 7 illustrates an alternative embodiment of the display 26 whereby the display 26 may articulate about a hinge or other connector so that it may be viewed from different angles. FIG. 8 illustrates embodiments of different features of the hand-held X-ray assembly 14. The top left figure of FIG. 8 shows alternative cursor styles that may be used to graphically indicate a position of a detected DR detector 40 with respect to the hand-held X-ray assembly 14. As described herein, a center indicating cursor 602, an outline cursor 604, or crosshairs 606 indicating a position of the corners of the DR detector 40 may be used, as well as other suitable cursor styles. The bottom left figure of FIG. 8 shows a video image 610 on the display 24 of the hand-held X-ray assembly 14 provided by its camera 26, wherein the collimator 76 aperture is being adjusted to narrow the radiation field as an operator prepares to capture an intra oral radiographic image. As shown on the display screen 24, the crosshair version of the DR detector position cursor 606 indicates that the detected DR detector 40 is centered. The bottom right figure of FIG. 8 shows a video image 611 on the display 24 of the hand-held X-ray assembly 14 provided by its camera 26, wherein the collimator 76 aperture is narrowed as desired around the cursors 606 and the X-ray source 150 of the hand-held X-ray assembly 14 is ready to be fired. The top right figure of FIG. 8 shows an illuminated radiation field on the patient using the light 26 in the hand-held X-ray assembly 14, which illumination may be used by the operator to initially position the hand-held X-ray assembly 14 or it may be used together with the display 24 cursors 602-606 described herein for positioning.

As disclosed herein, an X-ray source assembly may be attached to a boom of a mobile radiography system or to a stationary radiography system in an imaging room of a diagnostic medical facility. The boom may be used to selectively position the X-ray source assembly for irradiating with X-rays a desired imaging area of a subject as described herein. A camera may be attached to the boom or to the X-ray source assembly housing so that the camera travels together with the X-ray source assembly to be aimed in the same direction as the X-ray source emission to capture a moving image (video) of a radiation field on a subject to be imaged as the X-ray source is selectively manipulated by an operator until the radiation field coincides with the desired imaging area. The display screen receives the video transmission for display to an operator. The X-ray imaging system may include a mobile X-ray imaging system comprising a transport frame, wheels attached to the transport frame for rolling the transport frame along a floor, an adjustable column attached to and supported by the transport frame, an adjustable boom attached to and supported by the adjustable column. In another embodiment, the X-ray source assembly may be a hand-held X-ray source assembly having wireless communication capability and a display to quickly expose a patient and then receive and display a radiographic image captured by the exposure. The hand-held X-ray assembly may be particularly advantageous for dental radiographic imaging. A camera may also be included in the hand-held embodiment so that the camera travels together with the hand-held X-ray source assembly to be aimed in the same direction as the hand-held X-ray source emission to capture a moving image (video) of a radiation field on a subject to be imaged. The display screen may receive the video transmission for display to an operator.

As will be appreciated by one skilled in the art, aspects of the present invention may be embodied as a system, method, or computer program product. Accordingly, aspects of the present invention may take the form of an entirely hardware embodiment, an entirely software embodiment (including firmware, resident software, micro-code, etc.), or an embodiment combining software and hardware aspects that may all generally be referred to herein as a "service," "circuit," "circuitry," "module," and/or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

Program code and/or executable instructions embodied on a computer readable medium may be transmitted using any appropriate medium, including but not limited to wireless, wireline, optical fiber cable, RF, etc., or any suitable combination of the foregoing. The program code may execute entirely on the user's computer (device), partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer.

Computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified herein. These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified herein.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified herein.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A portable imaging apparatus comprising:
    an x-ray assembly enclosed by a housing configured to be held in one hand, the x-ray assembly comprising:
        an X-ray source within the housing configured to emit an X-ray beam;
        a light source within the housing configured to emit light;
        a collimator within the housing proximate the X-ray source and the light source, the collimator having an aperture to define an X-ray radiation field on a portion of a patient to be exposed by the emitted X-ray beam, and to define an illumination field, coinciding with the radiation field on said portion of the patient, to be illuminated by the emitted light; and
        a video camera within the housing configured to capture and communicate a video image of the illuminated radiation field on the portion of the patient, the video image captured through the aperture of the collimator; and
    a display on the housing communicatively connected to the video camera to receive and display the captured video image of the illuminated radiation field on the portion of the patient.

2. The apparatus of claim 1, wherein the collimator aperture comprises a variable aperture to adjust a size of the radiation field, and wherein the light source is configured so that a size of the illumination field is adjusted simultaneously with the size of the radiation field.

3. The apparatus of claim 2, wherein the radiation field is substantially equivalent to a field of view of the video camera.

4. The apparatus of claim 3, wherein the light source is configured to project a cursor within the illumination field such that the projected cursor is visible within the illumination field on the portion of the patient and is visible on the video display of the portion of the patient.

5. The apparatus of claim 2, wherein the video camera is positioned in the apparatus such that a side of the aperture facing the X-ray source is in a field of view of the video camera and is visible on the display.

6. The apparatus of claim 1, wherein the display includes a digital generated cursor configured to indicate a center of the radiation field.

7. The apparatus of claim 1, wherein the light source, the video camera, and the X-ray source are all disposed on one side of the collimator.

8. The apparatus of claim 1, wherein the apparatus is configured to detect a position of a radiographic detector prior to emitting the X-ray beam, and wherein the display comprises a cursor configured to indicate the detected position of the detector.

9. The apparatus of claim 8, wherein the cursor is configured to outline physical boundaries of the detector corresponding to the detected position of the detector.

10. The apparatus of claim 8, wherein the cursor is configured to indicate a detected tilt, skew, rotational position, or a combination thereof.

11. The apparatus of claim 8, further comprising:
    a wireless receiver for receiving a radiographic image captured by the detector in response to the X-ray beam and transmitted from the detector to the apparatus; and
    a frame buffer for storing the radiographic image, and connected to the display for displaying the radiographic image.

12. The apparatus of claim 9, wherein the cursor is configured to display physical locations of the corners of the detector corresponding to the detected position of the detector.

13. The apparatus of claim 9, wherein the cursor is configured to display physical locations of the sides of the detector corresponding to the detected position of the detector.

14. The apparatus of claim 1, wherein the video camera is positioned in the apparatus such that a central axis of the X-ray beam coincides with a center of a field of view of the video camera.

15. The apparatus of claim 1, wherein the display comprises an articulating screen, a touch screen, or a combination thereof.

16. A method of operating an X-ray system having a hand-held X-ray source assembly and a DR detector, a video camera and a collimator in the hand-held X-ray source assembly, and a display screen on the hand-held X-ray source assembly, the method comprising:
    viewing the display screen while manually supporting and aiming the video camera in the hand-held X-ray source assembly until a video image of a target portion of a subject appears in the display screen as captured by the video camera through an aperture in the collimator;
    activating an X-ray source in the hand-held X-ray source assembly to radiographically expose the target portion of the subject through the aperture in the collimator;
    capturing a radiographic image of the target portion of the subject in a digital detector exposed by the activated X-ray source;
    the digital detector transmitting the captured radiographic image to the hand-held X-ray source assembly; and
    displaying the captured radiographic image of the target portion of the subject on the display screen.

17. The method of claim 16, further comprising:
    activating a light source in the hand-held X-ray source assembly to illuminate the target portion of the subject through the aperture in the collimator.

18. The method of claim 16, further comprising:
    detecting a position of the digital detector and displaying one or more cursors on the display screen that indicate the detected position of the digital detector.

19. The method of claim 16, further comprising:
adjusting the aperture of the collimator in the hand-held X-ray source assembly to increase or decrease a size of the target portion of the subject to be radiographically exposed.

20. The method of claim 19, further comprising:
activating a light source in the hand-held X-ray source assembly to illuminate an area of the target portion of the subject through the aperture in the collimator; and
automatically adjusting the illuminated area of the target portion of the subject corresponding to the adjusted aperture of the collimator.

21. A hand held X-ray system comprising:
an X-ray source assembly that is activatable to emit X-rays toward an object;
a video camera to capture a video image of the object to be exposed to the emitted X-rays;
a DR detector behind the object to capture a radiographic image of the object exposed by the emitted X-rays;
means for detecting a position of the DR detector prior to activating the X-ray source; and
a video display screen on the hand-held X-ray source assembly, wherein the video display screen is configured to display simultaneously a video image of the object to be exposed to the emitted X-rays captured by the video camera and a cursor indicating the detected position of the DR detector prior to activating the X-ray source and to display the cursor and the video image of the object while an operator manually aims the hand held X-ray system toward the object.

22. The system of claim 21, wherein the video display screen is further configured to display at least a portion of the object to be exposed by the emitted X-rays prior to activating the X-ray source and while the operator manually aims the hand held X-ray system, to receive the radiographic image of the object captured by the DR detector after activating the X-ray source, and to display the radiographic image of the object captured by the DR detector.

* * * * *